(12) United States Patent
Ramanna

(10) Patent No.: US 12,127,790 B2
(45) Date of Patent: Oct. 29, 2024

(54) SYSTEM AND METHOD FOR DIRECT AND CONSENSUAL PUPILLARY LIGHT REFLEX STIMULATION

(71) Applicant: Srinivas Dorasala Ramanna, Bangalore (IN)

(72) Inventor: Srinivas Dorasala Ramanna, Bangalore (IN)

( * ) Notice: Subject to any disclaimer, the term of this patent is extended or adjusted under 35 U.S.C. 154(b) by 681 days.

(21) Appl. No.: 17/293,883

(22) PCT Filed: Nov. 20, 2019

(86) PCT No.: PCT/IN2019/000036
§ 371 (c)(1),
(2) Date: May 13, 2021

(87) PCT Pub. No.: WO2020/105062
PCT Pub. Date: May 28, 2020

(65) Prior Publication Data
US 2021/0330187 A1    Oct. 28, 2021

(30) Foreign Application Priority Data
Nov. 21, 2018    (IN) .............................. 201841043944

(51) Int. Cl.
*A61B 3/18*    (2006.01)
*A61B 3/00*    (2006.01)
*A61B 3/06*    (2006.01)

(52) U.S. Cl.
CPC .............. *A61B 3/18* (2013.01); *A61B 3/0008* (2013.01); *A61B 3/063* (2013.01)

(58) Field of Classification Search
CPC ......... A61B 3/18; A61B 3/0008; A61B 3/063; A61B 3/0025; A61B 3/113; A61B 3/10; A61B 5/163; A61B 3/112
USPC ........................................................ 351/206
See application file for complete search history.

(56) References Cited

U.S. PATENT DOCUMENTS

| 10,529,133 B2 * | 1/2020 | Mokuya .................. G06F 3/038 |
| 2013/0208241 A1 * | 8/2013 | Lawson ................. G06V 40/19 |
| | | 351/246 |

FOREIGN PATENT DOCUMENTS

WO    WO-2017091909 A1 *    6/2017    ........... A61B 3/0008

* cited by examiner

*Primary Examiner* — Mohammed A Hasan
(74) *Attorney, Agent, or Firm* — Spencer Fane LLP

(57) ABSTRACT

The various embodiments herein provide a system and method for direct and consensual pupillary light reflex stimulation without cross-contamination of contralateral eye. The embodiments also provides a portable and easy-to-use system and method for eye stimulation of pupillary response assessment for medical evaluation. The system is a portable and head-mounted goggles system is provided for eye stimulation of pupillary response assessment. The head-mounted goggles system comprises a visor, a pair of LEDs, a pair of well-arrangement and two cameras. The well-arrangements are designed in such a way that the LEDs provide a narrow light cone only to the eye under observation and prevents the contralateral eye from being stimulated. The cameras are independent of each other and are configured to capture images and transmit the images to a remote computing device through wired and/or wireless means.

14 Claims, 3 Drawing Sheets

SYSTEM AND METHOD FOR DIRECT AND CONSENSUAL PUPILLARY LIGHT REFLEX STIMULATION

CROSS-REFERENCE TO RELATED APPLICATIONS

The embodiments herein claim the priority of the Indian Provisional Patent Application filed on Nov. 21, 2018 with the number 201841043944 and entitled, "SYSTEM AND METHOD FOR DIRECT AND CONSENSUAL PUPILLARY LIGHT REFLEX STIMULATION", and subsequently filed as a PCT application on Nov. 20, 2019 with the number PCT/IN2019/000036, the contents of which are incorporated herein by the way of reference.

BACKGROUND

Description of the Related Art

The embodiments herein are generally related to a system and method for examination of human eyes. The embodiments herein are particularly related to a system and method for direct and consensual pupillary light reflex stimulation and gaze guidance during vestibular testing without fixation. The embodiments herein are more particularly related to a system and method for direct and consensual pupillary light reflex stimulation without cross-contamination of contralateral eye. The embodiments herein are also related to a system and a method for gaze guidance for a human without contamination by a fixation inducing stimulus.

Description of the Related Art

Pupillary light reflex estimation has been a frequently employed in clinical eyes test for centuries to assess the integrity of a key neural pathway. The test is generally performed in the clinic using a pen-torch and results are documented by visual observation. Currently, some tools are available for objective recording of the results and have been called pupillometry systems.

In direct light reflex method, light is flashed into the eye and the reflex constriction of the pupil is observed in the same eye. In indirect or consensual light reflex, the light is flashed in one eye and the pupillary constriction is observed in the other eye (known as contralateral eye). In current methods, it is observed that the results of pupillary light reflex assessment are contaminated if the participation of the unintended eye in stimulation is not reliably prevented.

The currently employed stimulation methods do not provide complete light sealing to avoid light traveling to the contralateral eye. The methods of placing a mechanical obstruction between the two eyes are not standardized due to the varying facial shapes and sizes of patients.

Hence, there is a need for a system and a method to provide a standardized system and method for direct and consensual pupillary light reflex stimulation without cross-contamination of contralateral eye. There is also a need for providing the system in a portable and easily usable form. During vestibular testing, there are certain protocols such as positional testing in which the eyes should not fixate. This is generally achieved by denial of vision by means of an opaque visor occluding the goggle worn by the subject. The disadvantage of this method is that the eyes tend to hover all around or take an eccentric position in the orbit precluding optimal assessment by eye tracking tools. Therefore, there is also a need to have a method which can guide gaze without introducing fixation.

The above-mentioned shortcomings, disadvantages and problems are addressed herein, and which will be understood by reading and studying the following specification.

OBJECT OF THE EMBODIMENTS HEREIN

The primary object of the embodiments herein is to provide a system and method for direct and consensual pupillary light reflex stimulation.

Another object of the embodiments herein is to provide a system and method for direct and consensual pupillary light reflex stimulation without cross-contamination of contralateral eye.

Yet another object of the embodiments herein is to provide a portable and easy-to-use system and method for eye stimulation of pupillary response assessment for medical evaluation.

Another object of the embodiments herein is to provide an integrated system for direct and consensual pupillary light reflex stimulation without cross-contamination of contralateral eye along with a plurality of other eye tests.

Another object of the embodiments herein is to separately stimulate the right and left eyes of the wearer of the apparatus to perform pupillometry on the wearer of the apparatus.

Another object of the embodiments herein is to enable the wearer of the apparatus to identify the direction at which to focus the eye in order to enable effective examination of the eye.

Another object of the embodiments herein is to enable the wearer of the apparatus to mimic convergence and divergence of eyes by illuminating the appropriate LEDs.

These and other objects and advantages of the embodiments herein will become readily apparent from the following summary and the detailed description taken in conjunction with the accompanying drawings.

SUMMARY

The following details present a simplified summary of the embodiments herein to provide a basic understanding of the several aspects of the embodiments herein. This summary is not an extensive overview of the embodiments herein. It is not intended to identify key/critical elements of the embodiments herein or to delineate the scope of the embodiments herein. Its sole purpose is to present the concepts of the embodiments herein in a simplified form as a prelude to the more detailed description that is presented later.

The other objects and advantages of the embodiments herein will become readily apparent from the following description taken in conjunction with the accompanying drawings.

The various embodiments herein provide a system and method for direct and consensual pupillary light reflex stimulation without cross-contamination of contralateral eye. The embodiments also provide a portable and easy-to-use system and method for eye stimulation of pupillary response assessment for medical evaluation.

According to one embodiment herein, a portable and head-mounted goggles system is provided for eye stimulation of pupillary response assessment. The head-mounted goggles system comprises a visor, a pair of LEDs, a pair of well-arrangement and two cameras. The pair of LEDs are placed at the well-arrangement in the head-mounted gear.

The well-arrangements are placed in such a way that the LEDs provide a narrow light cone only to the eye under observation and prevents the contralateral eye from being stimulated. The cameras are independent of each other and are configured to capture images and transmit the images to a remote computing device through wired and/or wireless means.

According to one embodiment herein, a head-mounted apparatus is provided for direct and consensual pupillary light reflex stimulation without cross-contamination of contralateral eye. The apparatus comprises a plurality of LED wells, a plurality of arrays of light emitting diodes (LEDs), a power source, electrical and electronic circuitry, a plurality of cameras, and a fastening mechanism for holding the apparatus in the head of a human user. The plurality array of LEDs is comprised in the plurality of LED wells. The electrical and electronic circuitry is configured to connect with an external computing device through wired and wireless means. The external computing device is configured to control the working of the apparatus. The plurality of cameras are configured to share the images captured to an external computing device connected to the apparatus through wired and wireless means.

According to one embodiment herein, the LED wells are designed to focus on the eyes of a wearer of the apparatus. The LED wells are designed such that when a plurality of LEDs in one of the LED wells is illuminated, the light does not illuminate any other LED wells. The LED wells are designed to provide a plurality of stimulation methods to the wearer's eye.

According to one embodiment herein, the plurality of arrays of LEDs is configured to light up individual LEDs in the array. The decision of illuminating a LED is determined based on the stimulation to be provided to the wearer's eye.

According to one embodiment herein, the plurality of LEDs in the arrays of LEDs is configured to separately stimulate the right and left eyes of the wearer of the apparatus. The separate stimulation enables performing pupillometry on the wearer of the apparatus.

According to one embodiment herein, the plurality of LEDs in the arrays of LEDs is configured to enable the wearer of the apparatus to identify the direction at which to focus the eye in order to enable effective examination of the eye. The wearer's eye is induced with a fixation for a plurality of examination techniques and the wearer's eye is provided with an intent to see without inducing fixation in a different set of plurality of examination techniques.

According to one embodiment herein, the plurality of LEDs in the arrays of LEDs is configured to enable the wearer of the apparatus to mimic convergence and divergence of eyes by illuminating the appropriate LEDs.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
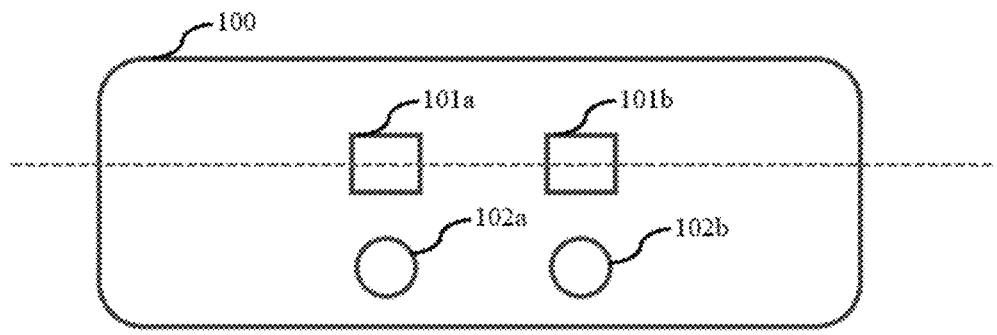
FIG. 1 illustrates a front-view of a head-mounted goggles system for eye stimulation of pupillary response assessment, according to an embodiment herein.

Although the specific features of the embodiments herein are shown in some drawings and not in others. This is done for convenience only as each feature may be combined with any or all of the other features in accordance with the embodiment herein.

DETAILED DESCRIPTION OF THE EMBODIMENTS HEREIN

In the following detailed description, a reference is made to the accompanying drawings that form a part hereof, and in which the specific embodiments that may be practiced is shown by way of illustration. These embodiments are described in sufficient detail to enable those skilled in the art to practice the embodiments and it is to be understood that other changes may be made without departing from the scope of the embodiments. The following detailed description is therefore not to be taken in a limiting sense.

The various embodiments herein provide a system and method for direct and consensual pupillary light reflex stimulation without cross-contamination of contralateral eye. The embodiments also provide a portable and easy-to-use system and method for eye stimulation of pupillary response assessment for medical evaluation.

According to one embodiment herein, a portable and head-mounted goggles system is provided for eye stimulation of pupillary response assessment. The head-mounted goggles system comprises a visor, a pair of LEDs, a pair of well-arrangement and two cameras. The pair of LEDs are placed at the well-arrangement in the head-mounted gear. The well-arrangements are placed in such a way that the LEDs provide a narrow light cone only to the eye under observation and prevents the contralateral eye from being stimulated. The cameras are independent of each other and are configured to capture images and transmit the images to a remote computing device through wired and/or wireless means.

According to one embodiment herein, a head-mounted apparatus is provided for direct and consensual pupillary light reflex stimulation without cross-contamination of contralateral eye. The apparatus comprises a plurality of LED wells, a plurality of arrays of light emitting diodes (LEDs), a power source, electrical and electronic circuitry, a plurality of cameras, and a fastening mechanism for holding the apparatus in the head of a human user. The plurality array of LEDs is comprised in the plurality of LED wells. The electrical and electronic circuitry is configured to connect with an external computing device through wired and wireless means. The external computing device is configured to control the working of the apparatus. The plurality of cameras are configured to share the images captured to an external computing device connected to the apparatus through wired and wireless means.

According to one embodiment herein, the LED wells are designed to focus on the eyes of a wearer of the apparatus.

The LED wells are designed such that when a plurality of LEDs in one of the LED wells is illuminated, the light does not illuminate any other LED wells. The LED wells are designed to provide a plurality of stimulation methods to the wearer's eye.

According to one embodiment herein, the plurality of arrays of LEDs is configured to light up individual LEDs in the array. The decision of illuminating a LED is determined based on the stimulation to be provided to the wearer's eye.

According to one embodiment herein, the plurality of LEDs in the arrays of LEDs is configured to separately stimulate the right and left eyes of the wearer of the apparatus. The separate stimulation enables performing pupillometry on the wearer of the apparatus.

According to one embodiment herein, the plurality of LEDs in the arrays of LEDs is configured to enable the wearer of the apparatus to identify the direction at which to focus the eye in order to enable effective examination of the eye. The wearer's eye is induced with a fixation for a plurality of examination techniques and the wearer's eye is provided with an intent to see without inducing fixation in a different set of plurality of examination techniques.

According to one embodiment herein, the plurality of LEDs in the arrays of LEDs is configured to enable the wearer of the apparatus to mimic convergence and divergence of eyes by illuminating the appropriate LEDs.

FIG. 1 illustrates a front-view of a head-mounted goggles system is for eye stimulation of pupillary response assessment. The system 100 comprises a pair of well-arrangements 101a, 101b and a pair of cameras 102a, 102b.

Figure 2:
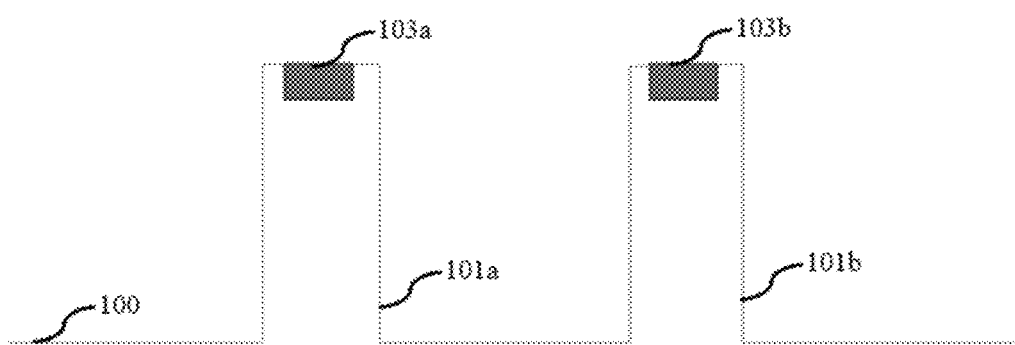
FIG. 2 illustrates a top-view of a head-mounted goggles system for eye stimulation of pupillary response assessment, according to an embodiment herein.

FIG. 2 illustrates a top-view of a head-mounted goggles system for eye stimulation of pupillary response assessment. The system 100 comprises a pair of well-arrangements 101a, 101b and a pair of LEDs 103a, 103b. The well-arrangements are designed in such a way that the LEDs provide a narrow light cone only to the eye under observation and prevents the contralateral eye from being stimulated. Each of the well-arrangements 101a, 101b has a depth that is larger than a width as illustrated in FIG. 2. In certain embodiments, the depth of the well-arrangements 101a, 101b is greater than about 2 times the width of the well-arrangements 101a, 101b. In certain embodiments, both of the well-arrangements 101a, 101b have a similar depth and both of the well-arrangements 101a, 101b have a similar width. As illustrated in FIG. 1, the camera 102a is outside of and adjacent to the well-arrangement 101a and the camera 102b is outside of and adjacent to the well-arrangement 101b.

Figure 3A:
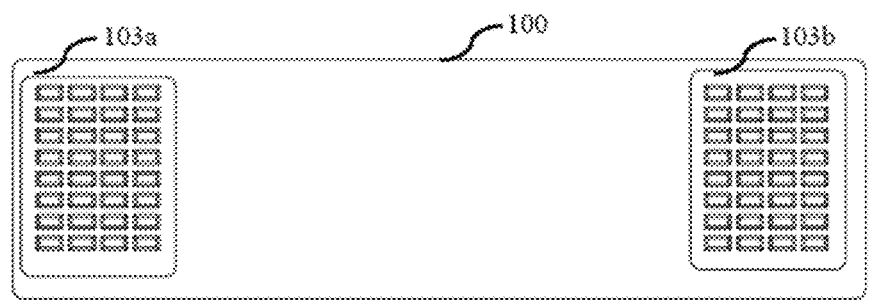
FIG. 3a illustrates a front-view of a head-mounted apparatus for eye stimulation of pupillary response assessment, according to an embodiment herein.

FIG. 3a illustrates a front-view of a head-mounted apparatus for eye stimulation of pupillary response assessment.

Figure 3B:
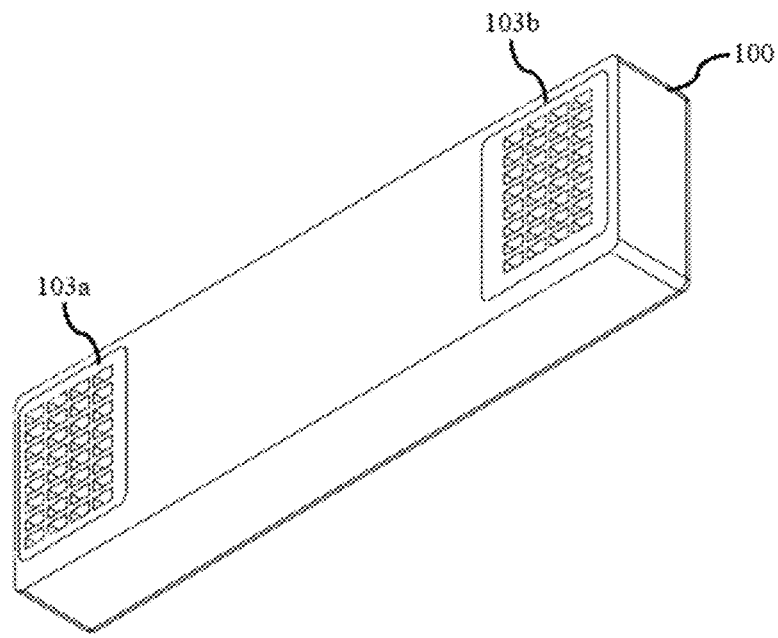
FIG. 3b illustrates a front-view of a head-mounted apparatus for eye stimulation of pupillary response assessment, according to an embodiment herein.

FIG. 3b illustrates a front-view of a head-mounted apparatus for eye stimulation of pupillary response assessment.

The various embodiments herein provide a system and method for direct and consensual pupillary light reflex stimulation without cross-contamination of contralateral eye. The embodiments also provide a portable and easy-to-use system and method for eye stimulation of pupillary response assessment for medical evaluation. The currently employed stimulation methods do not provide complete light sealing to avoid light traveling to the contralateral eye. The methods of placing a mechanical obstruction between the two eyes are not standardized due to the varying facial shapes and sizes of patients. The embodiments provide a portable and easy-to-use system and method for eye stimulation of pupillary response assessment for medical evaluation. The embodiments also provide an integrated system, for direct and consensual pupillary light reflex stimulation without cross-contamination of contralateral eye along, with a plurality of other eye tests.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the disclosure with modifications. However, all such modifications are deemed to be within the scope of the appended claims.

It is also to be understood that the following claims are intended to cover all of the generic and specific features of the embodiments described herein and all the statements of the scope of the embodiments which as a matter of language might be said to fall there between.

What is claimed is:

1. A head-mounted apparatus for direct and consensual pupillary light reflex stimulation of an eye of a human use without cross-contamination of a contralateral eye of the human user, the apparatus comprising:
    a plurality of LED wells;
    a plurality of arrays of light emitting diodes (LEDs), wherein the plurality array of LEDs is comprised in each of the plurality of LED wells;
    a power source;
    electrical and electronic circuitry, wherein the electrical and electronic circuitry is configured to connect with an external computing device through wired and wireless means, and wherein the external computing device is configured to control the working of the apparatus;
    a plurality of cameras, wherein the plurality of cameras is configured to share the images captured to an external computing device connected to the apparatus through wired and wireless means and wherein one of the plurality of cameras is outside of and adjacent to one of the plurality of LED wells; and,
    a fastening mechanism for holding the apparatus on a head of the human user.

2. The system according to claim 1, wherein the LED wells are designed to focus on the eyes of the human user of the apparatus, and wherein the LED wells are designed such that when a plurality of LEDs in one of the LED wells is illuminated, the light does not illuminate any other LED wells, and wherein the LED wells are designed to provide a plurality of stimulation methods to the eye of the human user.

3. The system according to claim 1, wherein the plurality of arrays of LEDs is configured to light up individual LEDs in the array, and wherein a decision of illuminating the LEDs is determined based on the stimulation to be provided to the eye of the human user.

4. The system according to claim 1, wherein the plurality of LEDs in the arrays of LEDs is configured to separately stimulate each of the eyes of the human user of the apparatus, and wherein the separate stimulation enables performing pupillometry on the human user of the apparatus.

5. The system according to claim 1, wherein the plurality of LEDs in the arrays of LEDs is configured to enable the human user of the apparatus to identify the direction at which to focus the eye in order to enable effective examination of the eye, and wherein the human user's eye is induced with a fixation for a plurality of examination techniques and the human user's eye is provided with an intent to see without inducing fixation in a different set of plurality of examination techniques.

6. The system according to claim 1, wherein the plurality of LEDs in the arrays of LEDs is configured to enable the human user of the apparatus to mimic convergence and divergence of the eyes by illuminating the appropriate LEDs.

7. The system according to claim 1, wherein each of the LED wells has a depth and a width and wherein the depth is greater than about 2 times the width.

8. A head-mounted apparatus for direct and consensual pupillary light reflex stimulation of an eye of a human use without cross-contamination of a contralateral eye of the human user, the apparatus comprising:
  a plurality of LED wells, wherein each of the LED wells has a depth and a width and wherein the depth is greater than about 2 times the width;
  a plurality of arrays of light emitting diodes (LEDs), wherein the plurality array of LEDs is comprised in each of the plurality of LED wells;
  a power source;
  electrical and electronic circuitry, wherein the electrical and electronic circuitry is configured to connect with an external computing device through wired and wireless means, and wherein the external computing device is configured to control the working of the apparatus;
  a plurality of cameras, wherein the plurality of cameras is configured to share the images captured to an external computing device connected to the apparatus through wired and wireless means; and
  a fastening mechanism for holding the apparatus on a head of the human user.

9. The system according to claim 8, wherein the LED wells are designed to focus on the eyes of the human user of the apparatus, and wherein the LED wells are designed such that when a plurality of LEDs in one of the LED wells is illuminated, the light does not illuminate any other LED wells, and wherein the LED wells are designed to provide a plurality of stimulation methods to the eye of the human user.

10. The system according to claim 8, wherein the plurality of arrays of LEDs is configured to light up individual LEDs in the array, and wherein a decision of illuminating the LEDs is determined based on the stimulation to be provided to the eye of the human user.

11. The system according to claim 8, wherein the plurality of LEDs in the arrays of LEDs is configured to separately stimulate each of the eyes of the human user of the apparatus, and wherein the separate stimulation enables performing pupillometry on the human user of the apparatus.

12. The system according to claim 8, wherein the plurality of LEDs in the arrays of LEDs is configured to enable the human user of the apparatus to identify the direction at which to focus the eye in order to enable effective examination of the eye, and wherein the human user's eye is induced with a fixation for a plurality of examination techniques and the human user's eye is provided with an intent to see without inducing fixation in a different set of plurality of examination techniques.

13. The system according to claim 8, wherein the plurality of LEDs in the arrays of LEDs is configured to enable the human user of the apparatus to mimic convergence and divergence of the eyes by illuminating the appropriate LEDs.

14. The system according to claim 8, wherein one of the plurality of cameras is associated with one of the LED wells and wherein the one of the plurality of cameras that is associated with the one of the LED wells is adjacent to the one of the plurality of LED wells.

* * * * *